(12) United States Patent
Güller et al.

(10) Patent No.: US 6,605,256 B1
(45) Date of Patent: Aug. 12, 2003

(54) DEVICE FOR CONDUCTING PLURALITY OF CHEMICAL, BIOCHEMICAL OR PHYSICAL PROCEDURES IN PARALLEL

(75) Inventors: Rolf Güller, Herznach (CH); Séraphin Munch, Rixheim (FR); Thomas Gees, Almens (CH); Hansjörg Tschirky, Ettingen (CH)

(73) Assignee: Chemspeed, Ltd., Augst (CH)

( * ) Notice: Subject to any disclaimer, the term of this patent is extended or adjusted under 35 U.S.C. 154(b) by 0 days.

(21) Appl. No.: 09/445,881

(22) PCT Filed: Jun. 11, 1998

(86) PCT No.: PCT/CH98/00253

§ 371 (c)(1),
(2), (4) Date: Feb. 22, 2000

(87) PCT Pub. No.: WO98/57738

PCT Pub. Date: Dec. 23, 1998

(30) Foreign Application Priority Data

Jun. 16, 1997 (CH) .............................. 1467/97

(51) Int. Cl.[7] .................................................. B01L 3/00
(52) U.S. Cl. ...................... 422/99; 422/101; 422/103; 422/104
(58) Field of Search .................. 422/99, 130, 131, 422/68.1, 101, 103, 104

(56) References Cited

U.S. PATENT DOCUMENTS

| 4,493,476 | A | | 1/1985 | Strickland et al. |
|---|---|---|---|---|
| 5,137,698 | A | | 8/1992 | Ansorge et al. |
| 5,503,805 | A | * | 4/1996 | Sugarman et al. ........ 422/131 |
| 5,538,694 | A | * | 7/1996 | Delius ..................... 422/131 |
| 6,042,789 | A | * | 3/2000 | Antonenko et al. ......... 422/99 |
| 6,126,904 | A | * | 10/2000 | Zuellig et al. ............ 422/130 |
| 6,149,869 | A | * | 11/2000 | Antonenko et al. ......... 422/99 |
| 6,190,619 | B1 | * | 2/2001 | Kilcoin et al. ............ 422/131 |

FOREIGN PATENT DOCUMENTS

| WO | 8910188 | 11/1989 |
|---|---|---|
| WO | 9317785 | 9/1993 |
| WO | 9324233 | 12/1993 |
| WO | 9709353 | 3/1997 |

* cited by examiner

Primary Examiner—Robert J. Warden, Sr.
Assistant Examiner—Brian Sines
(74) Attorney, Agent, or Firm—Selitto, Behr & Kim

(57) ABSTRACT

A device for carrying out a multiplicity of chemical, biochemical or physical processes in parallel has a plurality of switching blocks (1), to which a multiplicity of reaction vessels (5) are removably fastened. Liquids, gases and/or solids can be supplied to and/or extracted from the reaction vessels (5) through the switching blocks (1). Each switching block (1) comprises a gas duct plate (11) and a functional plate (12) which is arranged so that it can be displaced on it. The gas duct plate (11) has a multiplicity of through-holes, a gas duct and a multiplicity of gas duct holes extending from the gas duct to the functional plate (12) and the functional plate (12) has a multiplicity of through-holes and depressions open to the gas duct plate (11). Depending on the position of the plates, through-holes, depressions or sealing surfaces of the functional plate (12) are located opposite to through-holes and gas duct holes of the gas duct plate (11).

15 Claims, 7 Drawing Sheets

DEVICE FOR CONDUCTING PLURALITY OF CHEMICAL, BIOCHEMICAL OR PHYSICAL PROCEDURES IN PARALLEL

The present invention relates to a device for carrying out a multiplicity of chemical, biochemical or physical processes in parallel, as defined in the preamble of the independent claim 1.

In chemical research in the pharmaceutical industry and the universities, it is becoming more and more important to discover a large number of potential active ingredients and to test the latter thoroughly as quick as possible. Part of the chemical research, therefore, currently deals with combinatory chemistry, parallel synthesis and high-speed chemistry. In this work, the possibility of being able to employ known or new types of chemical reactions as widely as possible with the least possible amount of adaptation is of central importance.

In consequence, the most varied types of devices have been created for carrying out a multiplicity of chemical, biochemical or physical processes in parallel. All of these processes, however, are either only suitable for special applications or are too complicated in construction, too large or are not user-friendly and/or do not permit the individual process steps to be sufficiently automated.

Such a type of device is being marketed by the company Bohdan Europe, France, under the designation RAM Synthesizer BHD 1524. This device comprises a switching block to which a multiplicity of reaction vessels are removably fastened. Gases are supplied to and/or extracted from the reaction vessels through a gas duct in a reaction vessel fastening plate, and liquids are supplied and/or extracted by means of hollow needles through the switching block, the needles penetrating through septa arranged in the switching block and the septa forming a seal for the reaction vessels.

This device has the disadvantage that in order to shake the reaction vessels, the complete switching block, together with the reaction vessels, has to be transferred to a separate shaking device. Shaking during the supply of liquid, which is often necessary or even essential, is impossible. In addition, all the reactions are carried out under septa, which is problematic—particularly in the case of aggressive solvents—because the septa can be impaired by the solvents. This can lead to a loss of leak-tightness of the septa, on the one hand and to pollution of the reaction medium, on the other. In addition, the septa lose leak-tightness after a plurality of penetrations, so that the employment of vacuum or positive pressure without manual intervention is not possible to a sufficient extent. Furthermore, the reaction vessels cannot be completely opened and closed automatically.

In view of the disadvantages of the previously known devices, as described above, the invention is based on the following object. This is to create a device for carrying out, in parallel, a multiplicity of chemical, biochemical or physical processes of the type mentioned at the beginning, by means of which device a plurality of various process steps, in particular the employment of vacuum or positive pressure and the supply and extraction of liquids, gases and/or solids can be undertaken without the switching block or switching blocks having to be displaced or converted.

This object is achieved by means of the device according to the invention, as it is defined in the independent claim 1. Preferred embodiment variants are provided by the dependent claims.

The essence of the invention consists in the fact that in a device for carrying out a multiplicity of chemical, biochemical or physical processes in parallel, having at least one switching block to which are fastened a multiplicity of reaction vessels in a removable or fixed manner, it being possible for liquids, gases and/or solids to be supplied to and/or extracted from the reaction vessels through the switching block, the switching block comprises at least one gas duct plate with at least one gas duct and at least one adjacent functional plate, at least one of these plates being arranged so that it can be displaced relative to the other. The gas duct plate or plates and the functional plate or plates have through-holes, through-slots and/or depressions, which are respectively located opposite to one another in at least one plate position in such a way that a) gases and/or liquids can be supplied to or extracted from at least one reaction vessel via the gas duct or via at least one gas duct and b) gases, liquids and/or solids can be supplied to or extracted from at least one reaction vessel both through the gas duct plate or through at least one gas duct plate and through the functional plate or through at least one functional plate.

By means of this device it is possible, depending on the plate position, to supply or extract liquids or gases to or from all or individual reaction vessels via the gas duct or ducts and/or to generate a vacuum or a positive pressure in the reaction vessels and/or to supply or extract gases, liquids and/or solids through mutually opposite through-holes or through-slots in the gas duct plate or plates and in the functional plate or plates to or from the reaction vessels with or without pressure balance. The sealing of the reaction vessels takes place by the functional plate or at least one functional plate in certain plate positions, so that septa are not absolutely necessary. It is therefore possible to dispense with the employment of a septum or, in any event, it can be arranged in such a way that it is only used as a seal for the reaction vessels in certain plate positions. In consequence, it is possible to avoid the problems with the devices of the state of the art, as mentioned above and in which septa always form the seal of the reaction vessels.

Because of the functional plate or plates, various process steps can be carried out without the relevant switching block having to be displaced or converted. The functional plate or plates also permit a compact construction of the switching blocks.

A commercially obtainable sampler combined with a dilutor such as the Gilson ASPEC XL by the Gilson company, France, or another robot or another automatic unit, which may possibly be adapted to the switching blocks and reaction vessels according to the invention, can be used for operating these switching blocks and reaction vessels.

The reaction vessels are advantageously fastened to the switching block by means of movable connectors. The reaction vessels can then be shaken without the relevant switching block also moving. In addition, the whole weight of the reaction vessels, including contents, does not rest on the shaking device so that relatively weak shaking devices, which generate relatively small vibrations, suffice. Only this permits at all the employment of vibration-sensitive peripheral units, such as for example vibration-sensitive samplers, robots or other automatic devices for supplying and/or removing liquids and/or solids. Furthermore, an essential advantage resides in the fact that even during the shaking, a liquid or a solid can be supplied to and/or extracted from a reaction vessel without difficulty by means of a supply and/or extraction tool, such as for example hollow needles, grippers or spoons, which is not the case with the previously known devices.

Such connectors advantageously have a bellows between a part at the reaction vessel end and a part at the switching block end. As an alternative to the bellows, a flexible tube or a ball joint are, for example, conceivable.

For certain applications, a removable reflux condenser is preferably arranged between at least one of the reaction vessels and the switching block, which reflux condenser has a cooling tube, which extends sufficiently far into the reaction vessel for cooling to take place in the reaction vessel in the reaction vessel and reflux condenser connection region or below it. The cooling tube is then advantageously arranged in only one half of the cross section of the opening of the reaction vessel.

In this way, a liquid can be supplied to the reaction vessel, a protective gas, gaseous reactant, gaseous catalyst or a solid can be added to the reaction vessel and/or a pressure balance can be achieved, for example by means of a supply tool or via the gas duct or a gas duct, at the same time as the reflux condensing. All these interventions in the reaction vessel take place through the same opening, which contributes to the fact that the device according to the invention can be constructed in a relatively compact and low-cost manner and is maintenance-friendly and operator-friendly.

The device according to the invention for carrying out a multiplicity of chemical, biochemical or physical processes in parallel is described in greater detail below with reference to the attached drawings, using an embodiment example. In the drawings.

Figure 1:
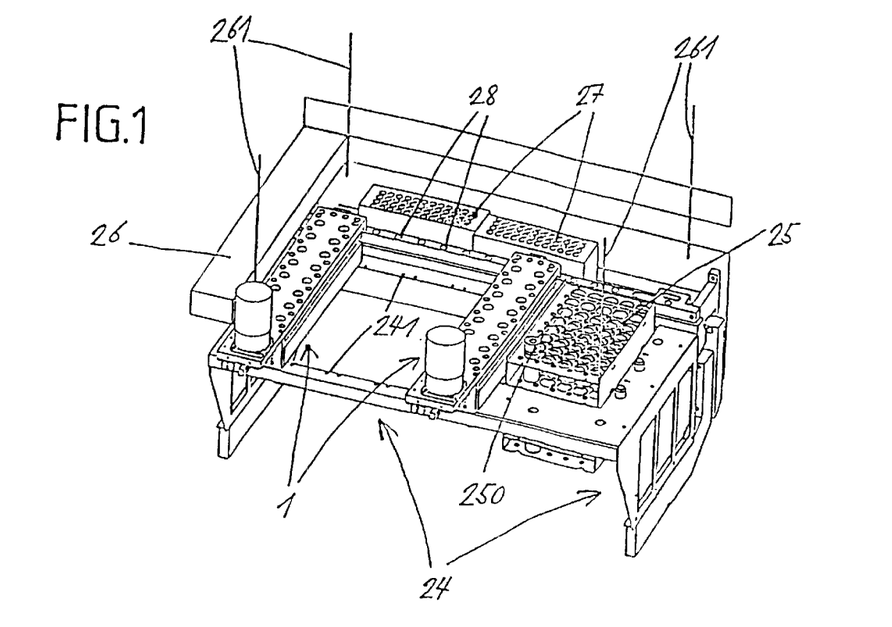
FIG. 1 shows a perspective view of an embodiment example of a device according to the invention for carrying out a multiplicity of chemical, biochemical or physical processes in parallel.

FIG. 1

The embodiment example shown, of a device according to the invention for carrying out a multiplicity of chemical, biochemical or physical processes in parallel, comprises a support frame 24, into which two switching blocks 1 are inserted, between which there is still space for three further switching blocks. The switching blocks 1 are fastened by means of screws, for which the support frame 24 has screw holes 241. An educt vessel frame 25, which is used for holding educt vessels 250, is also arranged on the support frame 24. Two holding blocks 27 or capture plates are provided for holding additional educt bottles or sample extraction bottles. Solvent extraction points 28 permit extraction of solvents from solvent tanks.

An arm 26 of a sampler is used to support a hollow needle for the handling of output materials or products. The corners of the access surface for the hollow needles are indicated by needles 261.

A shaking device, a vacuum pump, a plurality of gas supply devices, valves for the gas supply devices and the vacuum pump, cryostatic temperature regulators, a plurality of control units, a diluter and a multiplicity of reaction vessels are also part of the device but are not shown.

The following statement applies to the further description overall. If reference numbers are contained in a figure for the purpose of drawing clarity but are not mentioned in the directly associated descriptive text, reference is to be made to their mention in the previous descriptions of figures.

Figure 2:
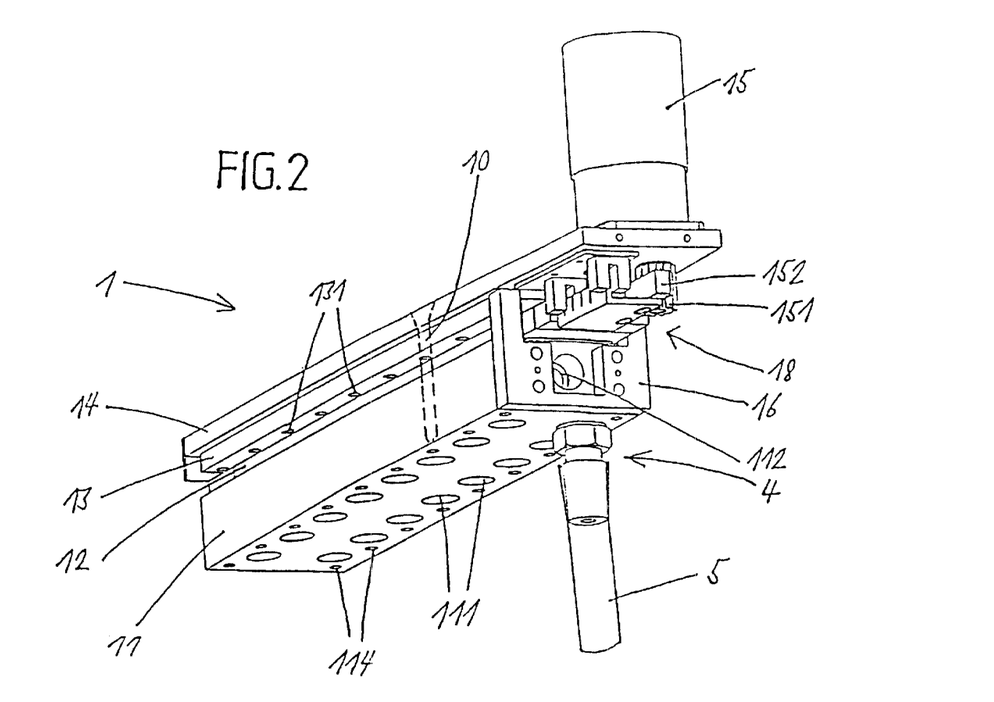
FIG. 2 shows a switching block of the device of FIG. 1 with a connector and a reaction vessel attached to it.
Figure 3:
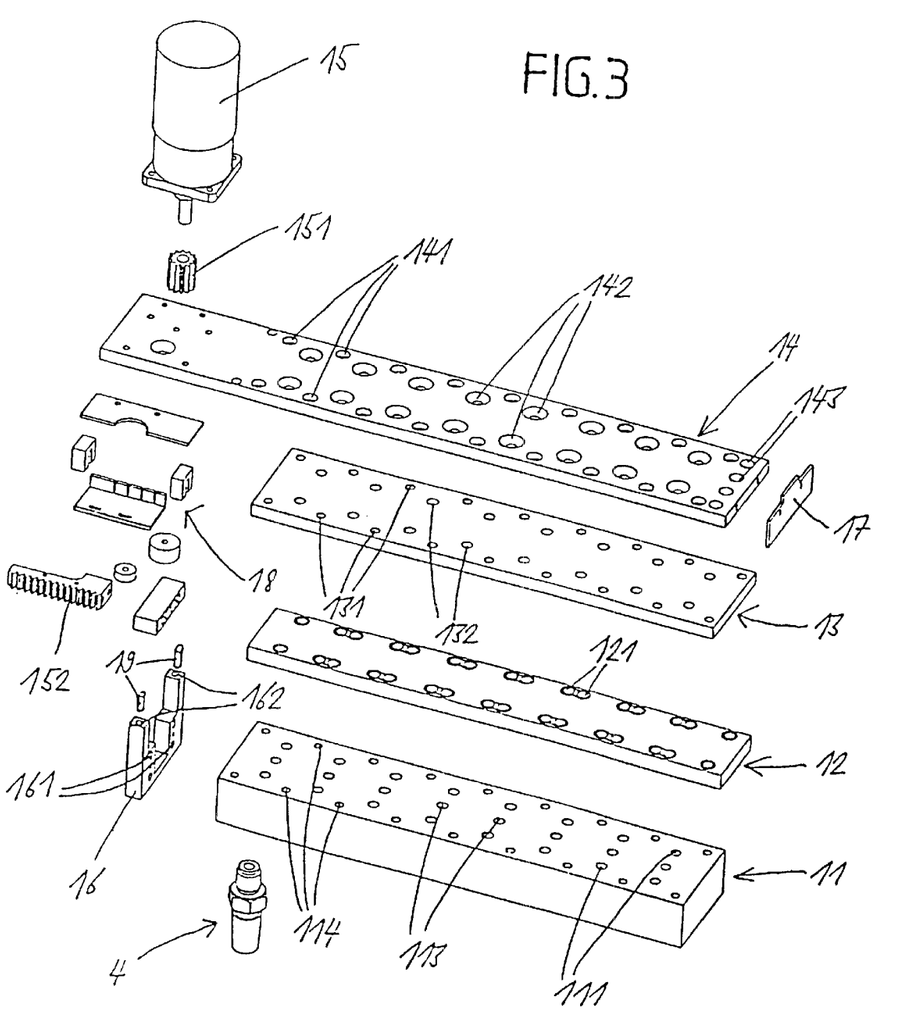
FIG. 3 shows the switching block with connector of FIG. 2, broken down into its individual parts.

FIGS. 2 and 3

A switching block 1 used in the device of FIG. 1 has a gas duct plate 11, a functional plate 12 in the form of a slide plate, a backing plate 13 and a support plate 14, which are located one above the other. The support plate 14, the backing plate 13 and the gas duct plate 11 are held together by screws 10, which are arranged in screw holes 141, 131 and 114. An end plate 16 with holes 162 for pins and screw holes 161 additionally connects these three plates by means of pins 19 and screws (not shown). The functional plate 12 is arranged so that it can be displaced between the gas duct plate 11 and the backing plate 13. It is driven by a stepper motor 15 via a pinion 151 and a rack 152. Fastening, distance and positioning elements are indicated by the reference number 18.

In addition to the screw holes 141, the support plate 14 also has two rows of through-holes 142, which permit a needle or some other solid object to penetrate the plate. This plate is mainly used for stabilization, for protection and for holding the drive device for the function plate 12. It has, in addition, a further four holes 143 under which light barriers are arranged. These can be used for controlling the motion of the functional plate, triggered for example by means of a needle. A panel 17 is used as the collecting point for the light barrier signals.

The backing plate 13 has screw holes 131 and through-holes 132, which are located opposite to the screw holes 141 and through-holes 142 of the support plate 14. It preferably consists of a high-quality material and, in particular, its side facing towards the functional plate 12 is made more exactly than the support plate 14.

The functional plate 12 is narrower than the backing plate 13 and the gas duct plate 11, so that it fits exactly between the connecting screws of these two plates and is also evenly guided by these connecting screws. It includes through-holes 121, whose rims are slightly raised relative to the plate surface and thus ensure a good seal. On the bottom, furthermore, it also has depressions which are explained in more detail below in association with FIG. 4.

In addition to the screw holes 114 and the through-holes 111, the gas duct plate 11 has gas duct holes 113, which end in a central gas duct 112. An appropriate number of vacuum pumps and gas supply devices can be connected to the open end of the gas duct 112 by means of a valve, preferably a multiple valve.

Between the backing plate 13 and support plate 14, it is also possible to arrange a septum composed of a material which can be penetrated by a needle, which septum acts as an additional, optional seal for the reaction vessel openings when the through-holes 111 and 121 of the gas duct plate 11 and functional plate 12, respectively, are located opposite to one another.

Connectors 4, which are described in more detail further below, are used for the removable fastening of reaction vessels 5 to the switching block 1. A reaction vessel 5 can be allocated to each through-hole 111 of the gas duct plate 11.

The individual parts of the switching block 1 and the connectors 4 can, for example, consist of metal (in particular stainless steel, brass or titanium alloys), glass (in particular $SiO_2$ glass), plastic (in particular Teflon, polypropylene or polyethylene), natural stone (in particular granite or gneiss), or ceramic (in particular $AlO_3$ or MACOR®).

Figure 4:
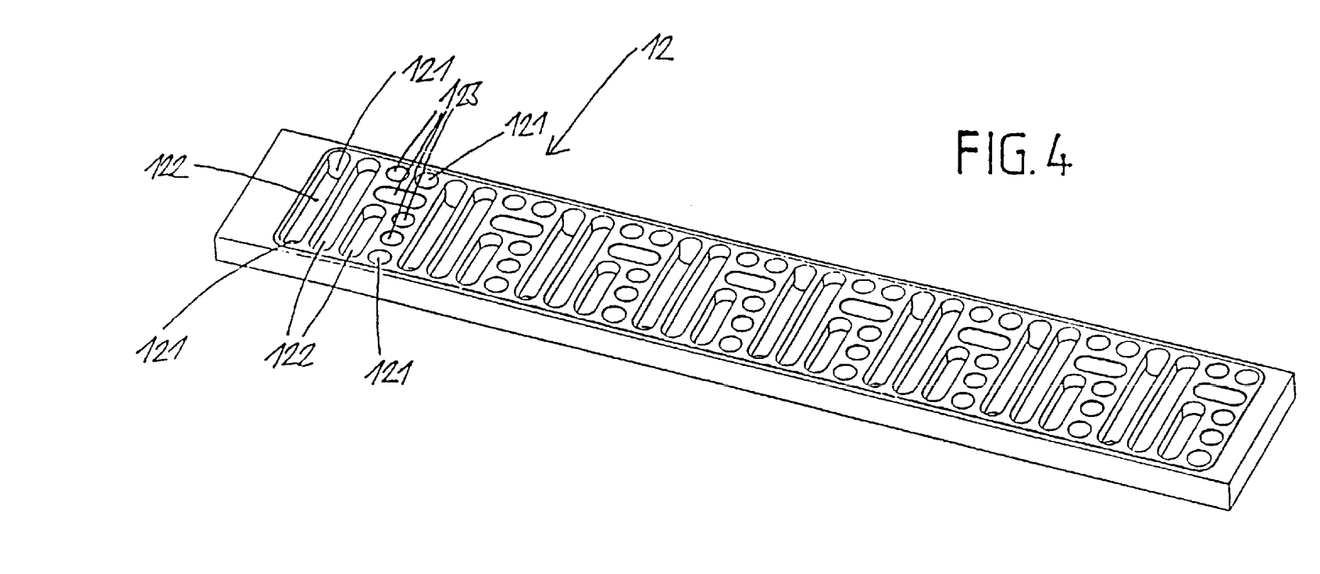
FIG. 4 shows the bottom of the functional plate of the switching block of FIG. 3.

FIG. 4

The bottom of the functional plate 12 has, in this case, a pattern which is repeated eight times. An individual pattern comprises four different arrangements of through-holes 121, depressions 122 and sealing surfaces 123 which, depending on the plate position, are located opposite the through-holes 111 and the gas duct holes 113 of the gas duct plate 11 and, by this means, define four different functional plate functions.

The first arrangement has two through-holes 121 and, between the latter, a depression 122. The first functional plate function therefore leaves both associated reaction vessels 5 completely open, i.e. both for supply and/or extraction tools and also relative to the gas duct 112.

In the second arrangement, a single long depression 122 is present. The second functional plate function closes off the two associated reaction vessels 5 for supply and/or extraction tools but leaves them open relative to the gas duct 112.

The third arrangement comprises a depression 122 and two sealing surfaces 123. The third functional plate function closes off an associated reaction vessel 5 completely, whereas it leaves the other associated reaction vessel 5 open relative to the gas duct 112 only.

In the fourth arrangement, two through-holes 121 and three depressions 122 are present. The fourth functional plate function leaves the two associated reaction vessels 5 open for supply and/or extraction tools but closes them off relative to the gas duct 112.

The rims of the through-holes 111, the depressions 122 and the sealing surfaces 123 are all slightly raised above the plate surface and therefore ensure a good seal.

Other arrangements of the through-holes 111, the depressions 122 and the sealing surfaces 123, and consequently other functional plate functions or other patterns, are of course conceivable.

Figure 5:
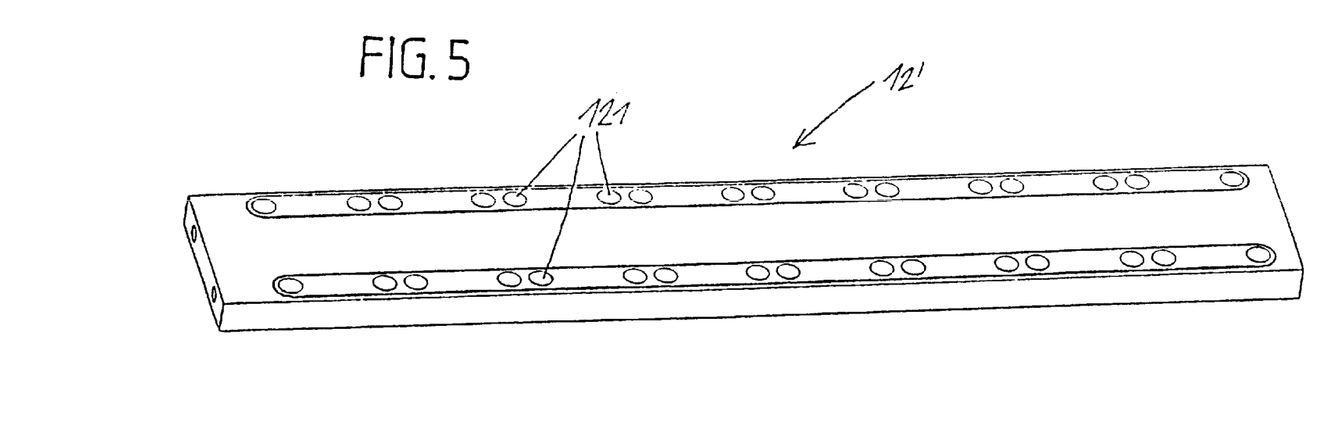
FIG. 5 shows an alternative embodiment variant of the top of the functional plate of the switching block of FIG. 3.

FIG. 5

This functional plate 12' differs from the functional plate 12 in FIG. 3 in that, on the top, it is not just the rims of the through-holes 121 which are raised above the surface of the plate but also the regions between the through-holes 121.

Figure 6:
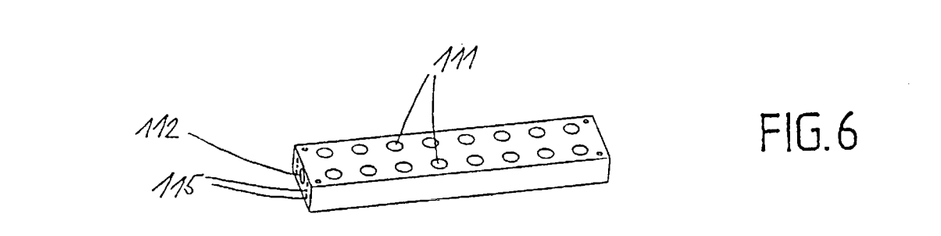
FIG. 6 shows the bottom of the gas duct plate of the switching block of FIG. 3.
Figure 7:
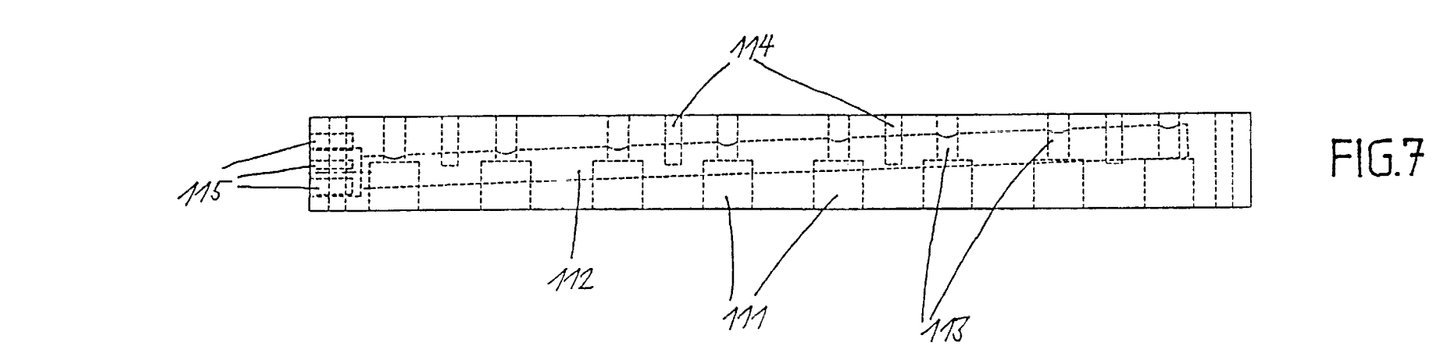
FIG. 7 shows a side view of the gas duct plate of FIG. 6, parts which are not visible being shown by broken lines.
Figure 8:
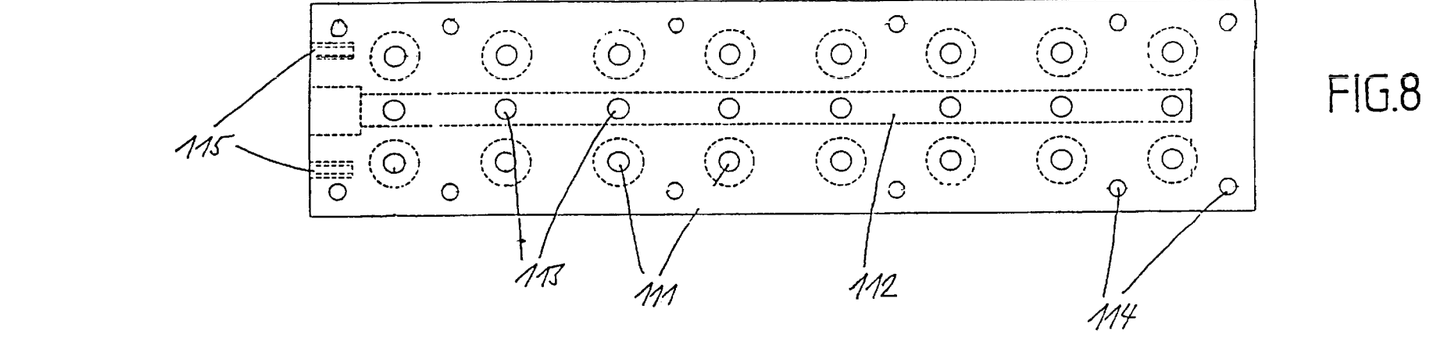
FIG. 8 shows a plan view of the gas duct plate of FIG. 6, parts which are not visible being shown by broken lines.

FIGS. 6–8

In order to ensure sufficient drainage of possibly condensing solvents as far as the closed end, the gas duct plate 11 shown has a central gas duct 112 which rises slightly from the open end and from which gas duct holes 113 extend to the plate surface facing towards the functional plate 12. The through-holes 111 are arranged in two parallel rows to correspond to the through-holes 132 of the backing plate 13 and the through-holes 142 of the support plate 14 and the screw holes 114 are arranged to correspond to the screw holes 131 and 141, respectively, of these plates. Screw holes for fastening the end plate 16 are indicated by 115.

A multiple valve, to which an appropriate number of vacuum pumps and devices for the supply of one or a plurality of gases is connected, is attached, for example screwed in, at the open end of the gas duct 112. A vacuum or a positive pressure can then be generated in the reaction vessels 5 and/or the most varied gases can be supplied to the reaction vessels 5. In this way, the atmospheres and conditions achievable by means of the functional plate functions can be multiplied in the reaction vessels 5.

Figure 9:
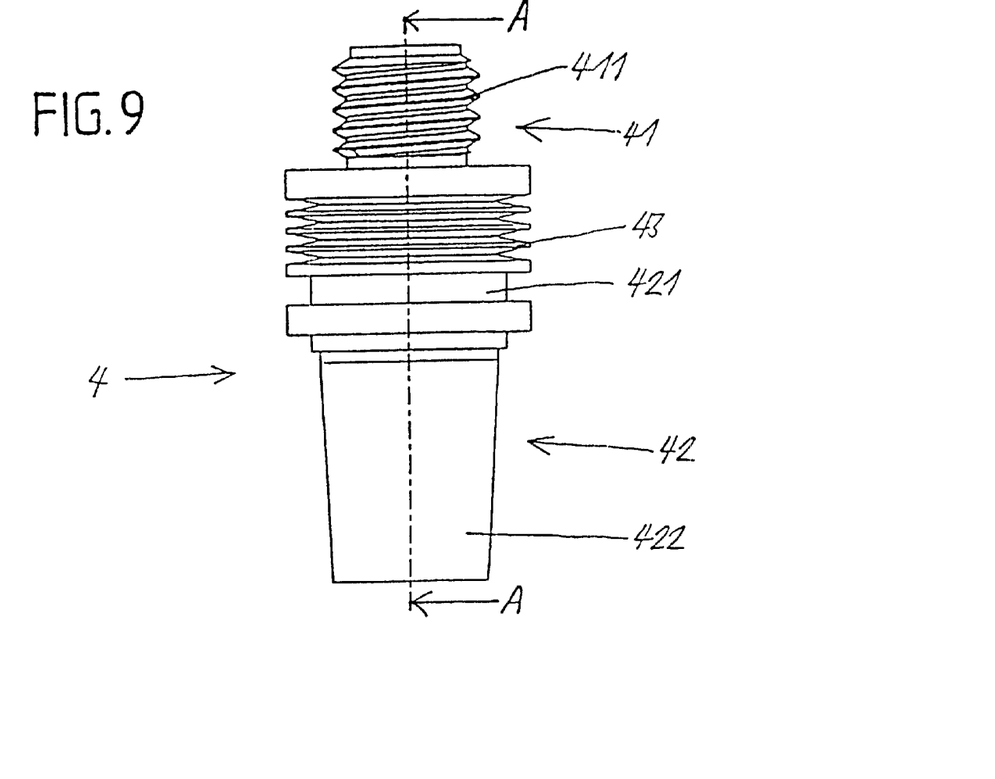
FIG. 9 shows a side view of a connector.
Figure 10:
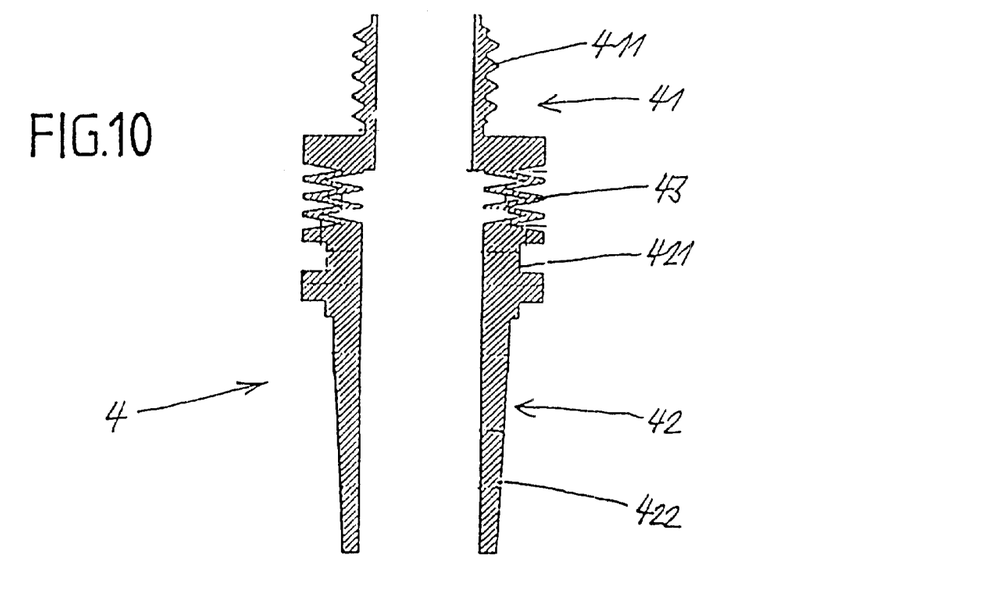
FIG. 10 shows a section through the connector of FIG. 9 along the line A—A.

FIGS. 9 and 10

The connector 4 shown comprises a part 41 at the switching block end and a part 42 at the reaction vessel end, between which is arranged a bellows 43 which ensures that the part 42 at the reaction vessel end can be moved relative to the part 41 at the switching block end. The part 41 at the switching block end is provided with a thread 411 so that the connector 4 can be screwed to a through-hole 111 of the gas duct plate 11, the through-hole 111 being provided with an internal thread in its lower part. The part 42 at the reaction vessel end comprises a fixing region 421 for the application of fastening clamps and a standard ground joint 422 for the releasable fixing of a reaction vessel 5 or a reflux condenser.

The connector 4 consists, for example, of Teflon.

Figure 11:
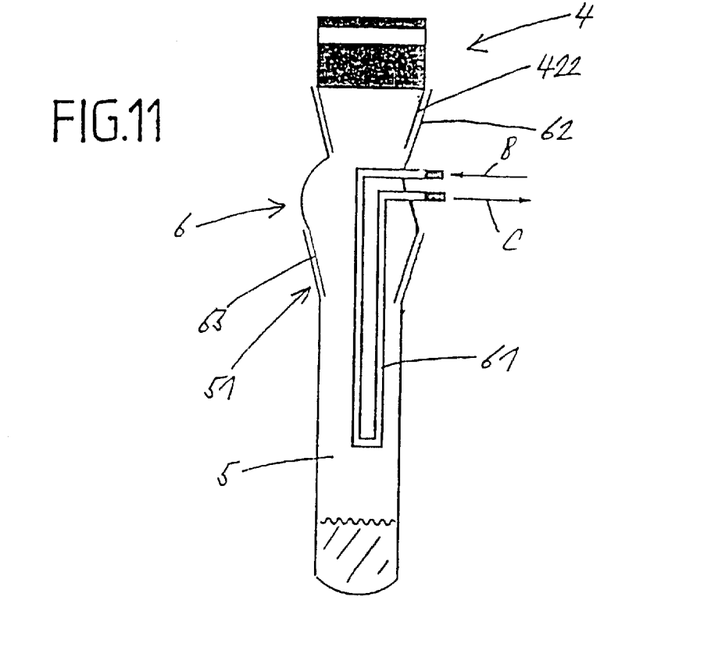
FIG. 11 shows a reflux condenser arranged between a reaction vessel and a connector.

FIG. 11

In its upper region, the reflux condenser 6 shown has a standard ground joint inner surface 62 for the releasable fastening of the reflux condenser 6 to the standard ground joint 422 of a connector 4 and, in its lower region, has a standard ground joint external surface 63 for the releasable fastening of a reaction vessel 5. It also includes a cooling tube 61, which extends sufficiently far into the reaction vessel 5 for cooling to take place in the reaction vessel 5 below the connection region 51 of the reaction vessel and reflux condenser. This achieves the effect that the gas phase condenses relatively far down in the reaction vessel 5 and the condensate remains in the reaction vessel 5.

The cooling tube 61 is arranged asymmetrically in the opening cross section of the reaction vessel 5, i.e. it is displaced towards the outside relative to the centre of the reflux condenser in order to create space for the introduction of a supply and/or extraction tool or the addition of, for example, a protective gas, gaseous reactants, gaseous catalysts or a solid, etc, into the reaction vessel 5. The supply and removal of the cooling medium, for example water, takes place as shown by the arrows B and C by means of flexible supply and removal lines, which are arranged and are connected to the supply and removal lines of the reflux condensers 6 of further reaction vessels 5 in such a way that their space requirement is minimized.

Figure 12:
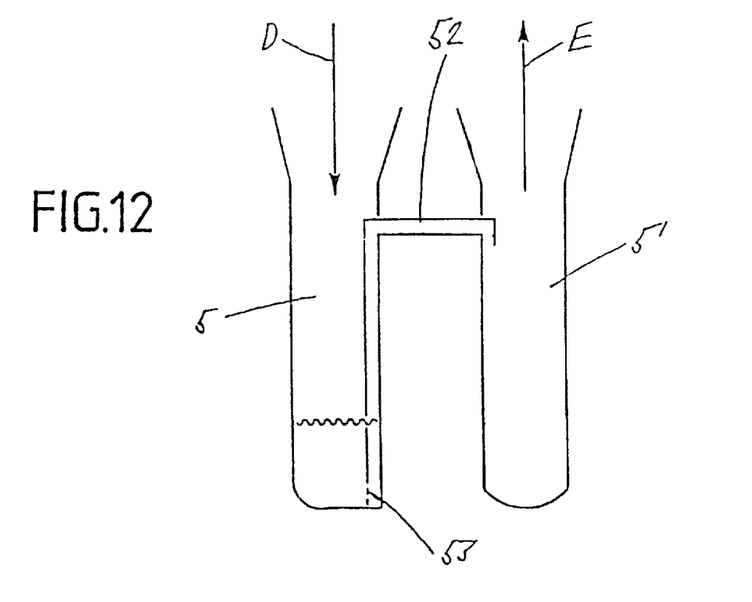
FIG. 12 shows two reaction vessels connected by a tube with a frit in one of the two reaction vessels and FIG. 13 shows a diagrammatic circuit diagram of a device according to the invention for carrying out a multiplicity of chemical, biochemical or physical processes in parallel.

FIG. 12

In the device according to the invention, many different types of reaction vessels 5 can, in principle, be used but they all have a connection possibility, such as a standard ground joint for example, for the releasable fastening of the reaction vessel 5 to, for example, a reflux condenser 6 or a connector 4. The shape and the acceptance volumes of the reaction vessels 5 can be varied over a wide range as a function of the available space and the desired number of reaction vessels 5 inserted adjacent to one another. As an example, cylindrical reaction vessels 5 with round or flat bottoms, round beakers, pointed beakers, etc, in particular with acceptance volumes of 0.5 ml–200 ml, can be considered.

It is also possible to use reaction vessels onto which is melted an additional chamber with an inlet and an outlet. These chambers can be used as cooling or heating chambers and are preferably connected to one another in a space-saving manner.

Two reaction vessels 5, 5', which are connected by a tube 52 and can be used for filtration, are shown here. The first end of the tube 52 protrudes into the upper region of the reaction vessel 5', whereas the second end is melted into a frit 53, for example a glass frit, in the bottom region of the reaction vessel 5. Filtration can be undertaken through the frit 53 by the generation of pressure in the reaction vessel 5, as shown by the arrow D, and/or by the generation of a vacuum in the reaction vessel 5', as shown by the arrow E.

The reaction vessels 5 and 5' can also be provided with additional cooling or heating chambers and/or with reflux condensers 6. Fundamentally, the most widely varying combinations of these elements with all the possible types of reaction vessel are conceivable.

Figure 13:
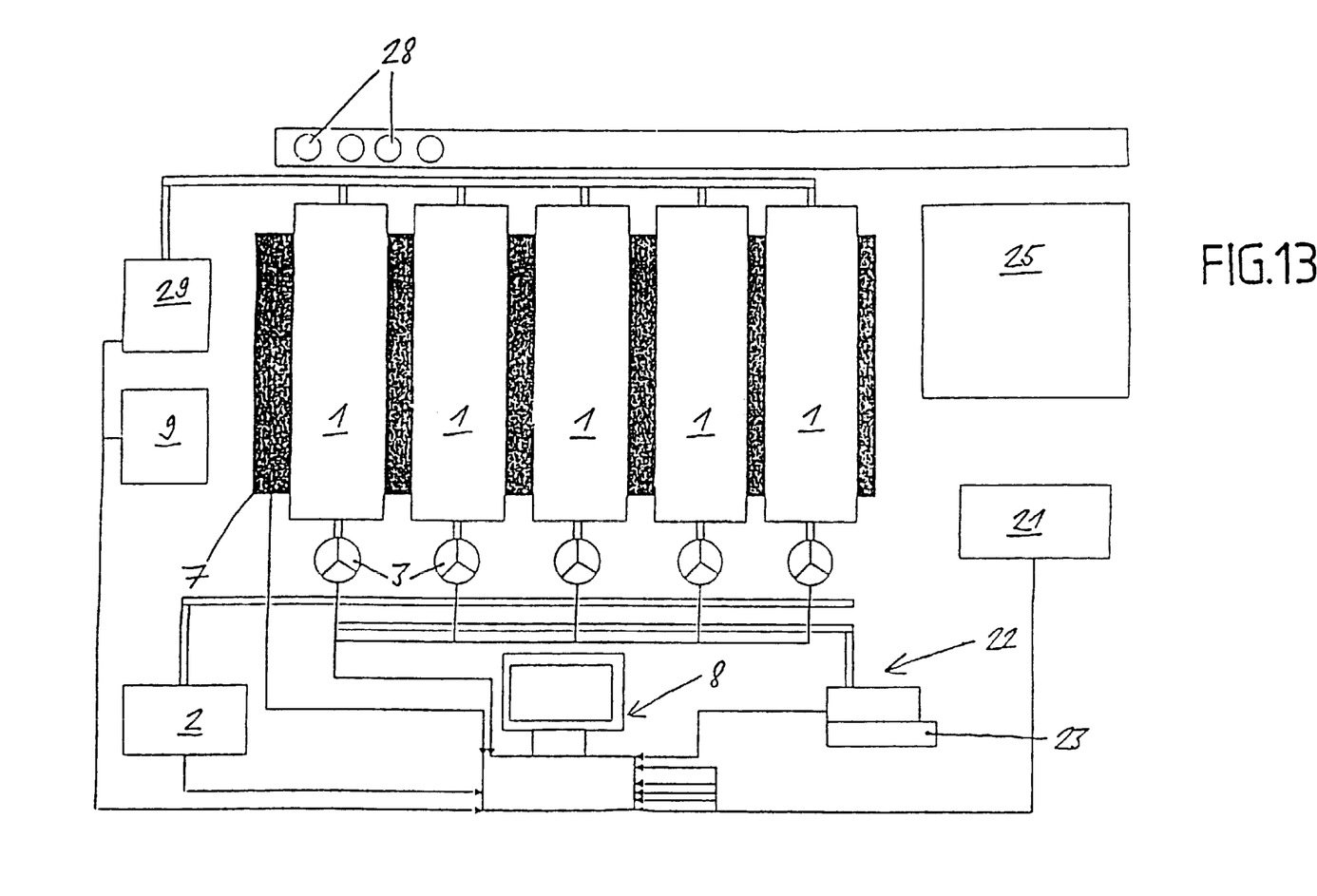

FIG. 13

The present embodiment example of a device according to the invention has five switching blocks 1, below which a shaking device 7 is arranged. The access to the gas duct 112 of the respective gas duct plate 11 is controlled by multiple valves 3, by means of which either a vacuum can be generated by a vacuum pump 2 or gas can be supplied or extracted by means of a device 22 for the supply or extraction of gas. In the embodiment example shown, the gas supply and extraction device 22 includes a tank 23 for a gaseous material, for example argon, hydrogen, etc.

Two cryostatic temperature regulators 9 and 29 are provided for supplying cooling media to the cooling tubes 61 of the reflux condensers 6 and to the melted-on cooling chambers of the reaction vessels.

The handling of the output materials or products takes place by means of a device 21 for the supply and extraction of liquids and/or solids, which device 21 comprises one or a plurality of hollow needles or other supply and/or extraction tools. The output materials or products are stored, in part, in vessels which are arranged in the vessel frame 25. Solvent or solution extraction points 28 permit extraction of solvents or solutions from tanks.

A control unit 8, for example a PC, is used for controlling the supply and extraction of liquids, gases and/or solids, i.e. for controlling the device 21 for the supply and extraction of liquids and/or solids, for controlling the device 22 for the supply and extraction of gases, for controlling the vacuum pump 2, the multiple valves 3 and the functional plates 12, together with their motors 15, and for controlling the shaking device 7 and the cryostatic temperature regulators 9 and 29.

In addition to the previously described device for carrying out a plurality of chemical, biochemical or physical processes in parallel, further design variations can be realized. The fact that the connections between the connectors 4, reflux condensers 6 and reaction vessels 5 do not necessarily have to be provided by means of standard ground joints but can also be provided by means of threads, face grinding, etc, is expressly mentioned here.

The device according to the invention permits the automation of a very wide range of chemical, biochemical or physical processes and their individual process steps. A large number of different, equivalent or similar processes can be carried out in parallel, in series, simultaneously or displaced in time.

What is claimed is:

1. Device for carrying out a multiplicity of chemical, biochemical or physical processes in parallel, having at least one switching block (1) to which are fastened a multiplicity of reaction vessels (5, 5') in a removable or fixed manner, it being possible for liquids, gases and/or solids to be supplied to and/or extracted from the reaction vessels (5, 5') through the switching block (1), wherein the switching block (1) comprises at least one gas duct plate (11) with at least one gas duct (112) and at least one adjacent functional plate (12), at least one of these plates being arranged so that it can be displaced relative to the other, and the gas duct plate (11) or plates and the functional plate (12) or plates have through-holes (111, 121), through-slots and/or depressions (122), which are located opposite to one another a) in at least one plate position in such a way that gases and/or liquids can be supplied to or extracted from at least two reaction vessels (5, 5') simultaneously via the same gas duct (112), and b) in at least another plate position in such a way that gases, liquids and/or solids can be supplied to or extracted from at least one reaction vessel (5, 5') both through the gas duct plate (11) or through at least one gas duct plate (11) and through the functional plate (12) or through at least one functional plate (12).

2. Device according to claim 1, wherein, in the case of at least one plate position, the through-holes (111, 121), through-slots and/or depressions (122) of the gas duct plate (11) or of at least one gas duct plate (11) and of the functional plate (12) or of at least one functional plate (12) are located opposite to one another in such a way that gases and/or liquids can be supplied to or extracted from at least one reaction vessel (5, 5') via the gas duct (112) or via at least one gas duct (112) and, at the same time, liquids and/or solids can be supplied or extracted both through the gas duct plate (11) or plates and through the functional plate (12) or plates.

3. Device according to claim 1 or 2, including exactly one functional plate (12) and one gas duct plate (11) per switching block, the functional plate (12) being arranged between the gas duct plate (11) and a backplate (13).

4. Device according to claim 1 or 2, wherein a septum composed of a material which can be penetrated by a needle is arranged on a support plate (14) or on the functional plate (12) or on a backplate (13).

5. Device according to claim 1 or 2, further comprising a drive, in particular a stepper motor (15), for displacing the functional plate (12) or plates.

6. Device according to claim 1 or 2, wherein a vacuum pump (2) is connected via a valve (3) to the gas duct (112) in order to generate a vacuum in the reaction vessels (5, 5'), the valve (3) being possibly a multiple valve, by means of which the gas duct (112) and the reaction vessels (5, 5') can be charged with at least one gas.

7. Device according to claim 1 or 2, wherein the reaction vessels (5, 5') are fastened to the switching block (1) by means of movable connectors (4), the connectors (4) possibly having a bellows (43), a flexible tube or a ball joint between a part (42) at the reaction vessel end and a part (41) at the switching block end.

8. Device according to claim 1 or 2, wherein a removable reflux condenser (6) is arranged between at least one of the reaction vessels (5) and the switching block (1), which reflux condenser (6) has a cooling tube (61), which extends sufficiently far into the reaction vessel (5) for cooling to take place in the reaction vessel (5) in the reaction vessel and reflux condenser connection region (51) or below it.

9. Device according to claim 8, wherein the cooling tube (61) is arranged in only one half of the cross section of the opening of the reaction vessel (5).

10. Device according to claim 1 or 2, wherein two of the reaction vessels (5, 5') are connected by a tube (52), the first of whose ends protrudes into one reaction vessel (5') and the second of whose ends is melted into a frit (53) in the other reaction vessel (5).

11. Device according to claim 1 or 2, further comprising a shaking device (7) and/or a stirring device, by means of which the reaction vessels (5, 5') can be shaken or stirred during the supply or extraction of liquids, gases and/or solids.

12. Device according to claim 1 or 2, further comprising a device (21, 22) for the supply and extraction of liquids, gases and/or solids, which device comprises one or a plurality of hollow needles.

13. Device according to claim 1 or 2, further comprising a control unit (8) for controlling the supply and extraction of liquids, gases and/or solids, for controlling the functional plate or plates (12) or their motors, for controlling the valve or the valves (3), for controlling the shaking device (7) or devices and/or for controlling one or a plurality of cryostatic temperature regulators (9, 29).

14. Device for carrying out a multiplicity of chemical, biochemical or physical processes in parallel, having at least one switching block (1) to which are fastened a multiplicity of reaction vessels (5, 5') in a removable or fixed manner, it being possible for liquids, gases and/or solids to be supplied to and/or extracted from the reaction vessels (5, 5') through the switching block (1), wherein each switching block (1) comprises a gas duct plate (11) with at least one gas duct (112) and an adjacent functional plate (12) that is arranged between the gas duct plate (11) and a backplate (13), at least one of the gas duct plate (11) and the functional plate (12) being arranged so that it can be displaced relative to the other, and the gas duct plate (11) or plates and the functional plate (12) or plates have through-holes (111, 121), through-slots and/or depressions (122), which are located opposite to one another a) in at least one plate position in such a way that gases and/or liquids can be supplied to or extracted from at least two reaction vessels (5, 5') simultaneously via the same gas duct (112), and b) in at least another plate position in such a way that gases, liquids and/or solids can be supplied to or extracted from at least one reaction vessel (5, 5') both through the gas duct plate (11) or through at least one gas duct plate (11) and through the functional plate (12) or through at least one functional plate (12).

15. Device for carrying out a multiplicity of chemical, biochemical or physical processes in parallel, having at least one switching block (1) to which are fastened a multiplicity of reaction vessels (5, 5') in a removable or fixed manner, it being possible for liquids, gases and/or solids to be supplied to and/or extracted from the reaction vessels (5, 5') through the switching block (1), wherein each switching block (1) comprises a gas duct plate (11) with at least one gas duct (112) and an adjacent functional plate (12) that is arranged between the gas duct plate (11) and a backplate (13), at least one of the gas duct plate (11) and the functional plate (12) being arranged so that it can be displaced relative to the other, and the gas duct plate (11) or plates and the functional plate (12) or plates have through-holes (111, 121), through-slots and/or depressions (122), which are located opposite to one another a) in at least one plate position in such a way that gases and/or liquids can be supplied to or extracted from at least two reaction vessels (5, 5') simultaneously via the same gas duct (112), and b) in at least another plate position in such a way that gases, liquids and/or solids can be supplied to or extracted from at least one reaction vessel (5, 5') both through the gas duct plate (11) or through at least one gas duct plate (11) and through the functional plate (12) or through at least one functional plate (12) and wherein c) in the case of at least one plate position, the through-holes (111, 121), through-slots and/or depressions (122) of the gas duct plate (11) or of at least one gas duct plate (11) and of the functional plate (12) or of at least one functional plate (12) are located opposite to one another in such a way that gases and/or liquids can be supplied to or extracted from at least one reaction vessel (5, 5') via the gas duct (112) or via at least one gas duct (112) and, at the same time, liquids and/or solids can be supplied or extracted both through the gas duct plate (11) or plates and through the functional plate (12) or plates.

\* \* \* \* \*